(12) United States Patent
Gerber

(10) Patent No.: US 7,593,777 B2
(45) Date of Patent: Sep. 22, 2009

(54) FIXATION OF A MEDICAL IMPLANT TO THE EXTERIOR OF A BODY ORGAN

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 830 days.

(21) Appl. No.: 10/973,944

(22) Filed: Oct. 26, 2004

(65) Prior Publication Data

US 2006/0089690 A1    Apr. 27, 2006

(51) Int. Cl.
*A61N 1/05* (2006.01)
(52) U.S. Cl. .............................. 607/115; 607/133; 606/1
(58) Field of Classification Search .................. 607/40, 607/115, 116, 133, 137; 604/891.1
See application file for complete search history.

(56) References Cited

U.S. PATENT DOCUMENTS

| | | |
|---|---|---|
| 4,736,749 A | 4/1988 | Lundback |
| 5,472,438 A * | 12/1995 | Schmit et al. .................. 606/1 |
| 5,580,569 A | 12/1996 | Giampapa |
| 5,766,234 A | 6/1998 | Chen et al. |
| 6,185,452 B1 | 2/2001 | Schulman et al. |
| 6,338,345 B1 | 1/2002 | Johnson et al. |
| 6,506,190 B1 | 1/2003 | Walshe |
| 6,510,332 B1 | 1/2003 | Greenstein |
| 6,626,919 B1 | 9/2003 | Swanstrom |
| 6,650,943 B1 | 11/2003 | Whitehurst et al. |
| 6,689,056 B1 | 2/2004 | Kilcoyne et al. |
| 6,735,474 B1 | 5/2004 | Loeb et al. |
| 7,020,531 B1 * | 3/2006 | Colliou et al. .............. 607/133 |

* cited by examiner

*Primary Examiner*—Carl H Layno
*Assistant Examiner*—Brian T Gedeon
(74) *Attorney, Agent, or Firm*—Shumaker & Sieffert, P.A.

(57) ABSTRACT

In general, invention is directed to devices and methods for use in laparoscopic surgical procedures in which a medical implant is affixed to or implanted within an exterior surface of a body organ. A system, for example, is described that includes a laparoscopic cannula and a delivery instrument disposed within the cannula to fix a medical implant to an exterior surface of an organ. The delivery instrument has a distal end including a cavity and a vacuum port to draw a portion of the exterior surface of the organ into the cavity. The medical implant is affixed to the portion of the exterior surface drawn into the cavity of the delivery instrument.

21 Claims, 6 Drawing Sheets

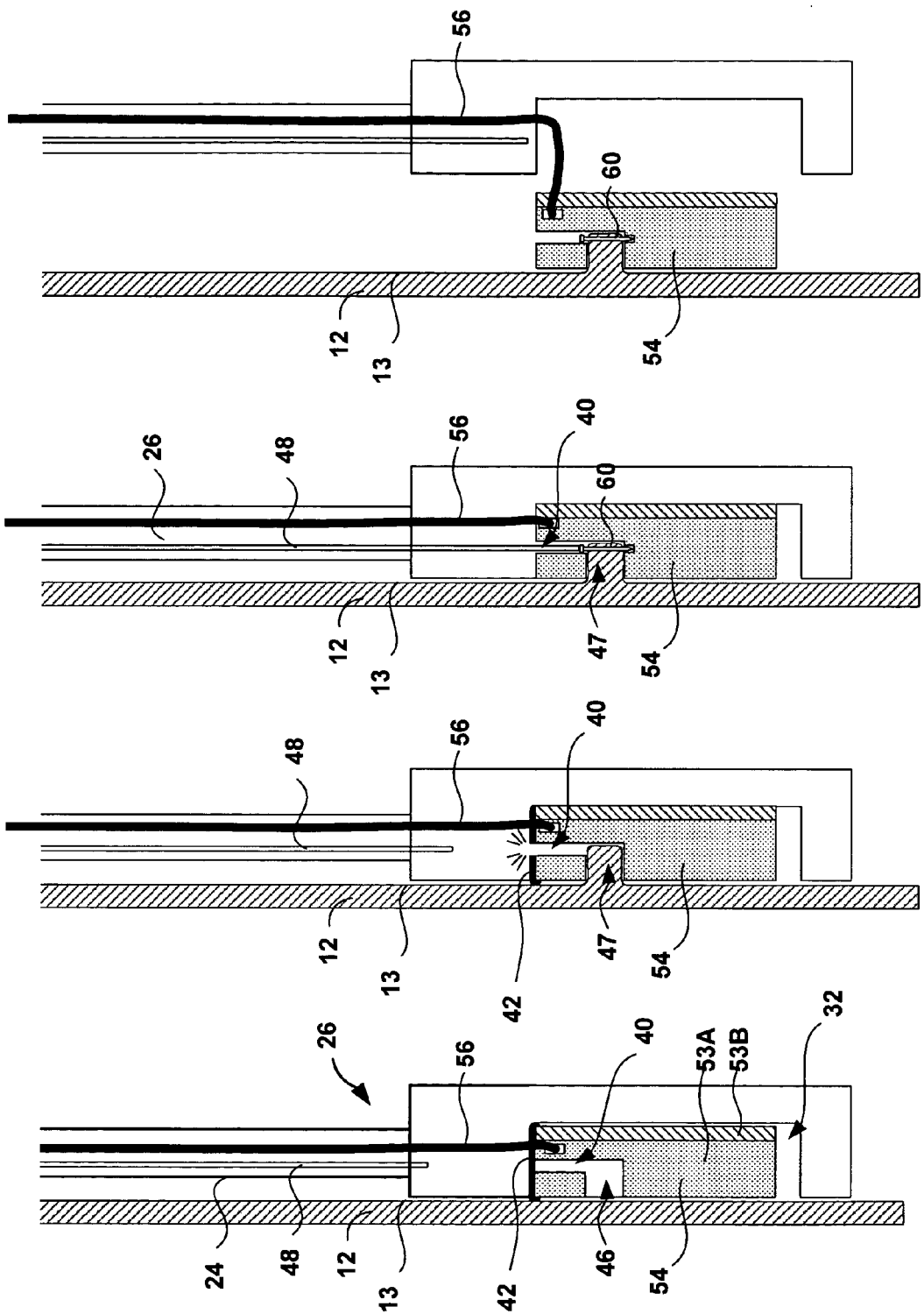

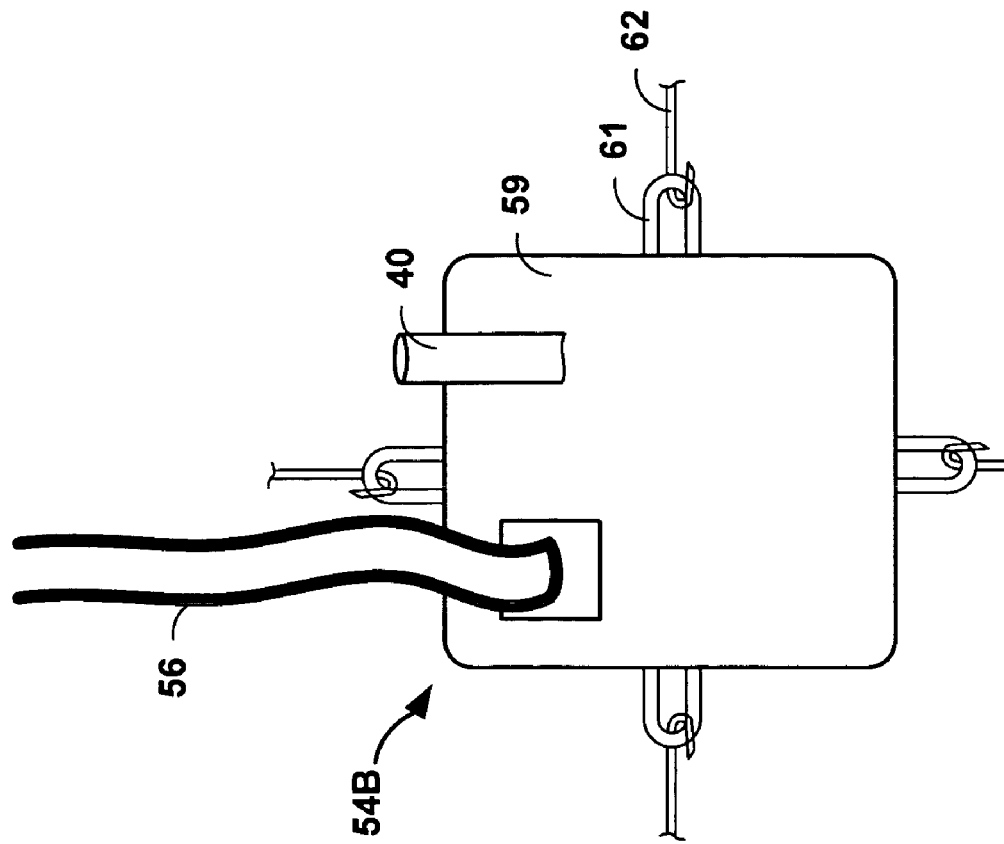
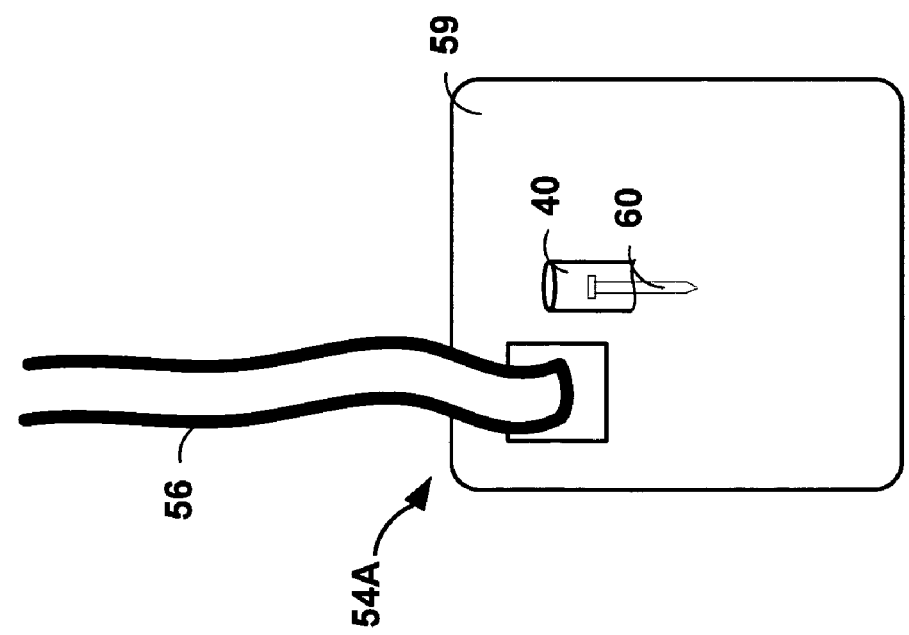

FIXATION OF A MEDICAL IMPLANT TO THE EXTERIOR OF A BODY ORGAN

TECHNICAL FIELD

The invention relates generally to surgical techniques, and, more particularly, to laparoscopic techniques for fixing a medical implant to an exterior surface of an organ.

BACKGROUND

A common surgical technique is a laparoscopic procedure in which, after administering a general anesthetic, a patient's abdomen is inflated with $CO_2$ or other inert inflammable gas. Rigid tubes with air-tight valve mechanisms ("trocars") are then inserted into the gas-filled abdominal cavity so that a video camera and other surgical instruments can be introduced into the abdomen. The video camera is typically deployed via an endoscope that projects a view of the abdomen onto a video monitor located in the operating room.

Laparoscopy surgery is used for a variety of reasons. In some situations, laparoscopic surgery is used to affix or implant a miniaturized medical device or circuit, drug bolus or other item or object on or within the exterior surface of an organ. As one example, U.S. Pat. No. 6,510,332 to Robert J. Greenstein describes an electrode which is designed and adapted for application by laparoscopic surgery. The electrode includes an attachment member which can be attached to body organs, even in cases where the organ is subject to vigorous, periodic peristaltic movement within the body (e.g., digestive organs).

As another example, U.S. Pat. No. 6,626,919 to Lee L. Swanstrom describes a laparoscopic technique in which a locking apparatus is used for securing an implant, such as a stent or stent graft, to a vessel or organ wall. Other examples include U.S. Pat. No. 5,766,234 to James C. Chen and U.S. Pat. No. 6,506,190 to Christopher J. Walshe that describe a flexible probe and a tissue anchor, respectively, that may be delivered via laparoscopic procedures. As yet another example, U.S. Pat. No. 5,580,569 to Vincent C. Giampapa describes a biodegradable therapeutic agent proportioned for laparoscopic delivery to a tumor or surgical site.

Table 1 below lists documents that disclose laparoscopic techniques and devices for delivery via such techniques.

TABLE 1

| Patent Number | Inventors | Title |
| --- | --- | --- |
| 6,510,332 | Robert J. Greenstein | Obesity treatment tools and methods |
| 6,626,919 | Lee L. Swanstrom | Method and apparatus for attaching or locking an implant to an anatomic vessel or hollow organ |
| 6,506,190 | Christopher J. Walshe | Tissue anchor system |
| 5,580,569 | Vincent C. Giampapa | Article for tissue-specific delivery of therapeutic agents |
| 5,766,234 | James C. Chen | Implanting and fixing a flexible probe for administering a medical therapy at a treatment site within a patient's body |

All documents listed in Table 1 above are hereby incorporated by reference herein in their respective entireties. As those of ordinary skill in the art will appreciate readily upon reading the Summary, Detailed Description and claims set forth below, many of the devices and methods disclosed in the patents of Table 1 may be modified advantageously by using the techniques of the present invention.

SUMMARY

The invention is directed to devices and methods for use in laparoscopic surgical procedures in which a medical implant is affixed to or implanted within an exterior surface of a body organ.

Various embodiments of the present invention provide solutions to one or more problems existing in the prior art with respect to laparoscopic delivery devices. The problems include, for example, inability of the delivery devices to adequately stabilize the exterior surface tissue of the organ, and inadequate feedback provided to the physician regarding proper positioning of the medical implantation to be delivered. These problems, in turn, can result in improper or insecure placement of an implant within the patient, undermining the efficacy or longevity of the implant.

Various embodiments of the present invention are capable of solving at least one of the foregoing problems. In general, the invention provides for methods and devices for vacuum-assisted laparoscopic delivery of the medical implant to the exterior surface of the body organ. The term "medical implant" is used herein to refer to any object that may be affixed to or implanted on an exterior of an organ via a laparoscopic procedure. For example, the medical implant may be an electrode for electrically stimulating the surface of the organ. As another example, the medical implant may comprise a diagnostic sensor or monitoring circuit for sensing one or more physiological conditions associated with the organ. The medical implant may also take the form of a therapeutic drug, an isotope for fixation on or near a cancerous region of an organ, or other composition that may be implanted via the laparoscopic procedure. The present invention may be utilized to laparoscopically deliver a medical implant to the surface of any of a number of body organs, including a patient's stomach, kidney or bladder.

The invention includes embodiments directed to a method comprising applying vacuum pressure to an exterior surface of an organ to draw at least a portion of the exterior surface into a cavity of a laparoscopic delivery instrument, and affix a medical implant to the portion of the exterior surface drawn into the cavity. The invention also includes embodiments directed to a system and a device that can perform laparoscopic delivery of a medical implant with a vacuum in accordance with the present invention. A system, for example, is described that includes a laparoscopic cannula and a delivery instrument disposed within the cannula to fix a medical implant to an exterior surface of an organ. The delivery instrument has a distal end including a cavity and a vacuum port to draw a portion of the exterior surface of the organ into the cavity. The medical implant is affixed to the portion of the exterior surface drawn into the cavity of the delivery instrument. In comparison to known techniques for fixation of implants to the exterior surface of an organ, various embodiments of the invention may provide one or more advantages. For example, various embodiments of the invention. For example, the application of vacuum pressure may be used to stabilize the exterior surface of the organ for improved fixation of the medical implant, e.g., by drawing tissue from the exterior surface into a chamber to permit attachment of medical implant.

The above summary is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A-3D are block diagrams illustrating a distal end of the laparoscopic delivery instrument of FIG. 2 when interacting with the exterior surface of an organ.

FIGS. 4A-4B are schematic diagrams illustrating top-views of embodiments of electrodes suitable for fixation to an exterior surface of a stomach or other organ.

DETAILED DESCRIPTION

Figure 1:
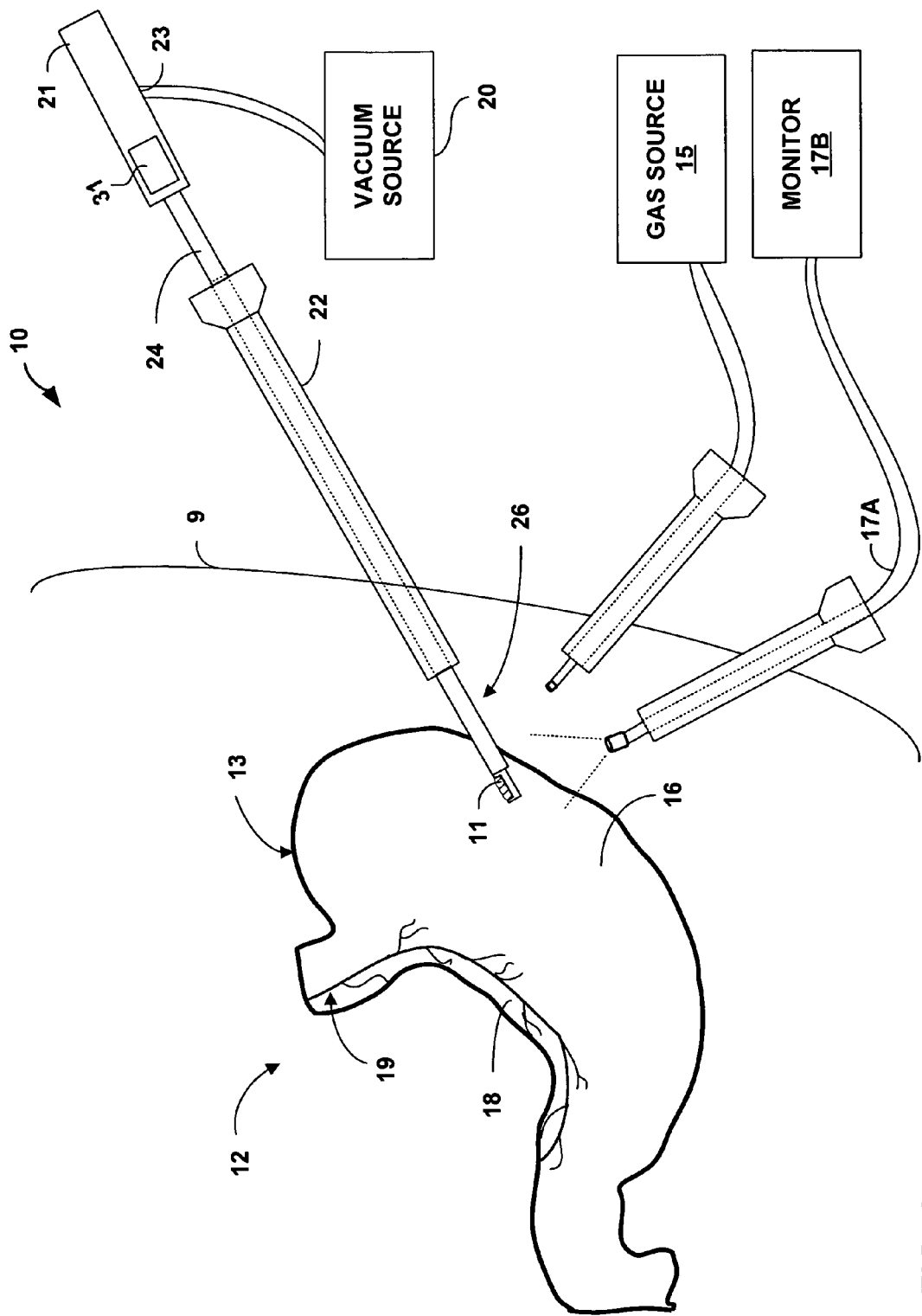
FIG. 1 is a schematic diagram illustrating a laparoscopic system for affixing a medical implant to an exterior surface of an organ.

FIG. 1 is a schematic diagram illustrating a laparoscopic fixation system 10 for affixing a medial implant 11 to the exterior surface 13 of a stomach 12. As shown in FIG. 1, the fixation system 10 uses a laparoscopic surgical technique to reach exterior surface 13 of stomach 12. In laparoscopic surgery, the patient receives general anesthesia and one or more small incisions are made in an abdomen 10 of the patient, usually via a trocar or other surgical instrument. Abdomen 10 is inflated with carbon dioxide or other inert gas from a gas source 15, and a video camera endoscope 17A is often inserted within the abdomen 9 so a surgeon can see the abdominal organs as displayed by monitor 17B. There are multiple targets for fixation of a medical implant to stomach 12 shown in FIG. 1, including, for example, a greater curvature 16, a lesser curvature 18, and a vagus nerve 19.

As shown in FIG. 1, the fixation system includes a laparoscopic delivery instrument 26 ("delivery instrument 26") to affix medical implant 11 to exterior surface 13 of stomach 12. As described herein, delivery instrument 26 applies a vacuum pressure to exterior surface 13 of stomach 12 to immobilize at least a portion of the exterior surface. Delivery instrument 26 then affixes medical implant 11 to the immobilized portion. Fixation of implant 11 may involve anchoring medical implant 11 to exterior surface 13 or implanting the implant below the exterior surface. Vacuum source 20 controls delivery of the vacuum pressure to delivery instrument 26, which includes tubular member 24 for conveying the vacuum pressure, and may be any conventional type of vacuum source suitable for delivering vacuum pressure to a laparoscopic surgical tool.

Delivery instrument 26 is inserted into an abdomen 10 of a patient through a cannula 22 during laparoscopic surgery. In general, cannula 22 is a flexible over-tube, and may be used with a trocar to provide an opening into the abdominal cavity of the patient. In that case, cannula 22 and delivery instrument 26 may be contained within the trocar, or the trocar may be removed prior to insertion of the delivery instrument.

Delivery instrument 26 is sized to fit within stomach 12 of the patient. Accordingly, cannula 22 is sized to fit within delivery instrument 26. Delivery instrument 26 may be flexible or curved to conform to a shape of the stomach at the target region. As will be described, delivery instrument 26 may comprise any of a variety of tools that apply vacuum pressure from vacuum source 20, and utilize the vacuum pressure for stabilization of the exterior surface of stomach 12 for fixation of medical implant 11, e.g., by drawing tissue from the exterior surface into a chamber to permit attachment of medical implant 11.

Delivery instrument 26 includes a proximal portion having a handle 21 and flexible tubular member 24 that extends from handle 21 into the body of the patient. Medical implant 11 is coupled to a distal end of delivery instrument 26 for fixation (i.e., anchorage or implantation) at a particular location of the exterior of stomach 12.

Delivery instrument 26 includes a vacuum inlet 23 on handle 21 to couple delivery instrument 26 to vacuum source 20. A vacuum outlet (not shown) at the distal end of delivery instrument 26 and, more particularly, at the interface between the delivery instrument and medical implant 11, applies the suction from vacuum source 20 to the exterior of the stomach in order to draw tissue into a chamber within distal end of delivery instrument 26. Distal end of delivery instrument 26 may apply the vacuum pressure, i.e., negative pressure, directly to exterior surface 13 of stomach 12 to draw the tissue into the chamber. Alternatively, delivery instrument 26 may apply the vacuum pressure through one or more voids within medical implant 11, causing the tissue of exterior surface 13 to draw into the chamber through the medical implant.

Delivery instrument 26 affixes medical implant 11 to the tissue drawn into the chamber, and disengages from medical implant 11, thereby leaving medical implant 11 attached to or implanted within exterior surface 13 of stomach 12. Delivery instrument 26 may, for example, advance a locking pin through the tissue drawn into the chamber of delivery instrument 26 to anchor medical implant 11 to the exterior of stomach 12. Alternatively, delivery instrument may inject medical implant 11 into the tissue drawn into the chamber.

In some embodiments, delivery instrument 26 may detect pressure variances within a pressure sensitive chamber within delivery instrument 26 to assist the surgeon in determining whether medical implant 11 is properly positioned on the exterior surface 13 of stomach 12. The distal end of delivery instrument 26 may, for example, be formed from a flexible material such that outside pressure applied to the distal end of the instrument by stomach 12 causes the flexible portion to deform, thereby varying the pressure within the instrument. Delivery instrument 26 may include a display 31 to output an indication of the pressure experienced by the distal end of the delivery instrument, thereby providing an indication of whether medical implant 11 is properly engaged with exterior surface 13. This indication, along with the a visualization endoscope, provide guidance to the surgeon for proper placement of implant 11.

As described further below, medical implant 11 may be any of a variety of implantable objects suitable for fixation to the exterior surface of stomach 12. For example, medical implant 11 may be an electrode for electrically stimulating the surface of stomach 12. The electrode may be coupled to an elongated lead carrying an electrical conductor to receive electrical stimulation energy from an implanted pulse generator designed for gastric stimulation, or may be self contained to include a pulse generator and a wireless transceiver for communication of sensed data to an external monitor or diagnostic device. As another example, medical implant 11 may comprise a diagnostic sensor or monitoring circuit for sensing one or more physiological conditions associated with the stomach 12, such as pressure, pH, temperature, fullness or other conditions. In some embodiments, implant 11 may be a sensor or strain gauge for monitoring peristaltic activity. Medical implant 11 may also take the form of a biologic or a therapeutic drug. The biologic or drug may be selected to delivery a therapy for a condition, or to selectively kill diseased or cancerous tissue, e.g., for chemotherapy. As another example, medical implant 11 may take the form of a radioactive isotope for fixation on or near a cancerous region of stomach 12 to support radiation therapy.

For ease of illustration, the invention is shown in reference to fixation of medical implant 11 to exterior surface 13 of stomach 12. However, the techniques described herein may be utilized to affix medical implant 11 to an exterior surface of other organs, including a bladder, small or large intestines, kidney or other organ of a body.

Figure 2:
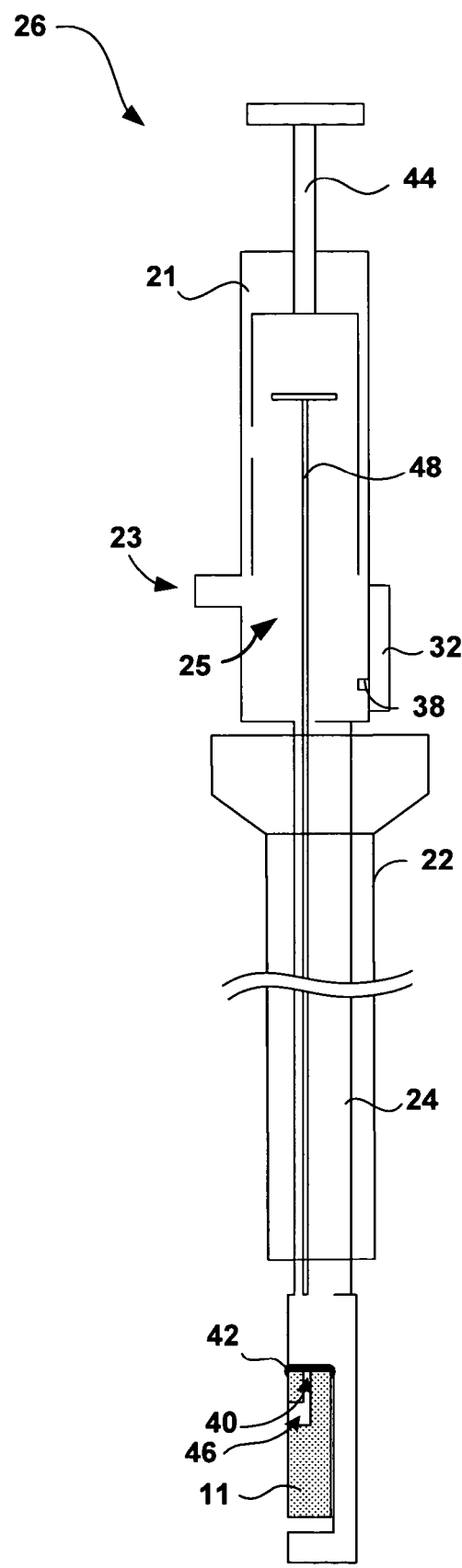
FIG. 2 is a schematic diagram illustrating an exemplary laparoscopic delivery instrument for fixing a medical implant to an exterior surface of an organ.

FIG. 2 is a schematic diagram illustrating an exemplary embodiment of delivery instrument 26 (FIG. 1) in further detail. In the illustrated embodiment, delivery instrument 26 includes handle 21 and flexible tube member 24 that extends from handle 21. Medical implant 11 is coupled to a distal end of probe 26 for delivery to an exterior surface of an organ, such as stomach 12 of FIG. 1. Specifically, delivery instrument 26 delivers medical implant 11 to the appropriate location along stomach 12 and anchors or implants medical implant 11 at the appropriate location.

In the illustrated example, delivery instrument 26 is capable of measuring pressure variation within a pressure sensitive chamber in order to assist the surgeon in laparoscopically fixing medical implant 11 to the stomach. Specifically, delivery instrument 26 includes a pressure sensor 38 to detect pressure variations within a pressure sensitive chamber of delivery instrument 26. Delivery instrument 26 further includes a display 32 located on handle 21 that displays the pressure measurements made by pressure sensor 38. As described above, display 32 may display pressure measurements with varying accuracy depending on the application. For example, display 32 may display relative pressure variations, e.g., using a number of LEDs that successively light up as the pressure increases. Pressure sensor 38 can comprise, for example, a piezoelectric pressure sensor, a capacitive pressure sensor, or any other sensor capable of detecting pressure variations. Handle 21 further incorporates appropriate electronics (not shown) to process the signals generated by pressure sensor 38 and drive display 32.

Vacuum inlet 23 receives pressure from vacuum source 20 (FIG. 1), and conveys the vacuum pressure to an inner portion 25 of delivery instrument 26 to form a pressure sensitive chamber. The pressure sensitive chamber may be controlled within delivery instrument 26 by closing a vacuum inlet 23 and covering vacuum outlet 40 with a membrane 42. Delivery instrument 26 may include a controller 44 on handle 21 to assist in opening and closing of vacuum inlet 23 and, thus, application of suction from vacuum inlet 23. Controller 44 may further control the pressure monitoring capabilities of delivery instrument 26. In particular, controller 44 may be utilized to active and deactivate power pressure sensor 38 and display 32. For example, controller 44 may close vacuum inlet 23 and activates pressure sensor 38 and display 32 before probe 26 of delivery instrument 26 is introduced into an abdomen of a patient through cannula 22 during laparoscopic surgery. In certain embodiment, controller 44 may comprise a plunger that is successively pushed through different stages to perform sequential operations during the delivery of medical implant 11 to the appropriate location along stomach 12. Alternatively, controller 44 may comprise a dial, switch, or similar control mechanism that can be switched to different settings to perform different functions.

Membrane 42 covering vacuum outlet 40 may be constructed of a flexible material such as flexible plastic. Membrane 42 can be adhered over vacuum outlet 40 during manufacture of delivery instrument 26. Membrane 42 prevents air from escaping via vacuum outlet 40, in turn, making the pressure sensitive chamber airtight.

Membrane 42 within the distal end of probe 26 deforms due to pressure variations experienced by the exterior surface of stomach 16. For example, when the distal end of probe 26 is being inserted and forced against the exterior surface, membrane 42 deforms due to an increased pressure caused by the application force, causing a pressure variation within the pressure sensitive chamber. Pressure sensor 38 detects the pressure variation within the pressure sensitive chamber, i.e., the pressure variation caused by the deformation of the distal end of probe 26, and delivery instrument 26 conveys the pressure variation via display 32 to a user. In this manner, delivery instrument 26 provides an indication of the amount of force applied to the exterior surface of the stomach, thereby providing an indication of whether medical implant 11 is properly positioned for fixation to the surface.

Upon identifying the appropriate location for placement of medical implant 11, controller 44 opens vacuum inlet 23 and deactivates, i.e., shuts off, the pressure detection functionality of delivery instrument 26. Vacuum inlet 23 receives sufficient suction pressure from vacuum source 20 to cause membrane 42 that covers vacuum outlet 40 to be removed. In other words, the suction pressure from vacuum sources 20 opens vacuum outlet 40 by opening, removing or rupturing membrane 42. Membrane 42 covering vacuum outlet 40 may be completely removed by the suction pressure. For example, the suction pressure may have a larger force than the adhesive holding membrane 42 over vacuum outlet 40. Alternatively, the suction of the vacuum may, instead, rupture membrane 42 in order to open vacuum outlet 40.

Upon removal or rupture of membrane 42, the suction from vacuum source 20 is further applied to vacuum outlet 40 to draw a portion of exterior surface 13 of stomach 12 into a void 46 of medical implant 11. Upon drawing the exterior surface tissue of stomach 12 into void 46, controller 44 is adjusted to cause delivery instrument 26 to affix medical implant 11 to the tissue. For example, controller 44 can be adjusted to cause a shaft 48 to advance a locking pin (not shown) through the surface tissue within void 46 in order to anchor medical implant 11 to the exterior of stomach 12. If controller 44 comprises a plunger, the plunger may be actuated into handle 21 in order to advance the locking pin through the tissue. However, any type of anchoring mechanism may be used to anchor medical implant 11 to the tissue, such as a staples or sutures. In other embodiments, controller 44 can be adjusted to affix medical implant 11 to exterior surface 13 of stomach 12 by partially or entirely implanting the medical implant within the tissue drawn into void 46. Once medical implant 11 is affixed to the exterior surface, the medical implant detaches from delivery instrument 26, thereby leaving the medical implant attached to the organ, e.g., the stomach.

FIGS. 3A-3D are block diagrams illustrating side views of one embodiment of a distal end of delivery instrument 26. Particularly, FIGS. 3A-3D illustrate the distal end of delivery instrument 26 in operation to affix a medical implant (i.e., an electrode 54 having a conductive lead 56, a conductive material 53A and an insulative backing 53B in this example) to the exterior surface 13 of the stomach.

FIG. 3A illustrates the distal end of delivery instrument 26 positioned proximal to exterior surface 13 of stomach 12. In the illustrated embodiment, the distal end of delivery instrument 26 includes a chamber 32 sized to hold electrode 34. Delivery instrument 26 further includes membrane 42 covering a vacuum port 40 formed within electrode 34 to provide a pressure sensitive cavity 46, also referred to as a "void," for use in fixing electrode 54 to exterior surface 13 of stomach 12.

Tubular member 24 provides a conduit for conveying a vacuum pressure created by vacuum source 20 (FIG. 1) to cavity 46. The vacuum pressure removes or ruptures membrane 42, as shown in FIG. 3B. As a result, delivery instrument 26 draws a portion 47 of the exterior surface 13 of stomach 12 into cavity 46 of electrode 54.

FIG. 3C illustrates anchoring of electrode 54 to the exterior surface 13 of stomach 12 via advancement of a locking pin 60 by shaft 48 through the portion 47 of the surface drawn into cavity 46 of electrode 54. During this process, the vacuum pressure maintains the draws tissue into contact with the electrical surface of electrode 54 to stabilize the tissue and ensure secure electrical contact. Locking pin 60 may comprise any of a variety of biocompatible structural materials which are well known in the medical art, such as stainless steel, titanium, high density polyethylenes, nylon, PTFE, or other material.

FIG. 3D illustrates the detachment of electrode 54 from delivery instrument 26. As illustrated in FIG. 3D, lead 56 remains coupled to electrode 54 and disposed within delivery instrument 26. Delivery instrument 26 is withdrawn from the abdominal cavity of the patient, and lead 56 is then removed from the delivery instrument and utilized in the desired manner, e.g., to sense electrical activity or deliver electrical stimulation to the exterior surface 13 of stomach 12. For example, lead 56 may be guided or tunneled to a pulse generator, which also is implanted within the patient. In other embodiments, lead 56 may extend from a diagnostic sensor to a monitoring device, which is implanted within or external to the patient.

FIG. 4A is a schematic diagram illustrating a top-view of an electrode 54A suitable for fixation to an exterior surface of stomach 12 or other organ. In the example embodiment of FIG. 4A, electrode 54A includes an electrically conductive surface 59, a vacuum port 40 to receive a vacuum pressure and apply the vacuum pressure to a bottom surface of the electrode, and a conductive lead 56. As illustrated in FIG. 4A, locking pin 60 remains disposed within vacuum port 40, thereby anchoring electrode 54A to a portion of the exterior surface of stomach 12 (not shown) drawn up into cavity 46 of the electrode.

FIG. 4B is a schematic diagram illustrating a top-view of another exemplary electrode 54B suitable for fixation to an exterior of stomach 12. In certain embodiments, as shown in FIG. 4B, electrode 54B has one or more eyelets 61, which serves to hold respective suture 62, string, staples, or other securing structures, which can secure the electrode to exterior surface 13 of stomach 12. Utilization of vacuum pressure to draw tissue into a cavity of electrode 54B may be advantages to ensure a secure, stable contact between electrode 54B and the tissue during the suturing process. A conventional laparoscopic suturing mechanism may be deployed to secure sutures 62. Many other possible attachments mechanisms, such as one or more polymeric filament, surgical adhesive, loops, rings, brackets, tacks, hooks, clips, strings, threads, or screws, can be utilized to facilitate the attachment or fixation of electrode 54 to the exterior surface of the stomach or another organ.

Figure 5A:
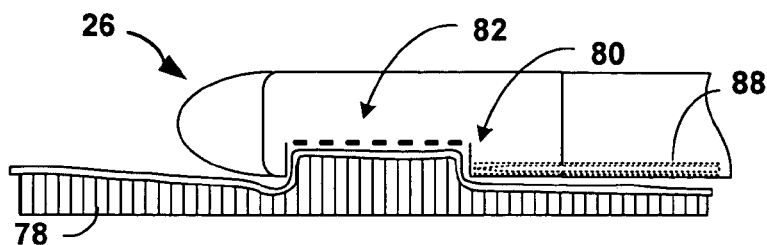
FIGS. 5A-5D are schematic diagrams showing another embodiment of a distal end of a delivery instrument for use in implant of a capsule within an exterior surface of an organ.

FIGS. 5A-5D are schematic diagrams showing another embodiment of a distal end of delivery instrument 26. Specifically, FIGS. 5A-5D illustrate a vacuum-assisted laparoscopic technique for implantation of a medical implant, i.e., a capsule 79 in this example, within an exterior surface of an organ. FIG. 5A depicts exterior tissue 78 of an organ drawn into a cavity 80 by vacuum pressure applied via one or more vacuum ports 82. Unlike the embodiments illustrated in FIGS. 3A-3D, vacuum ports 82 apply vacuum pressure directly to surface tissue 78 without utilizing a vacuum port of the medical implant.

Figure 5B:
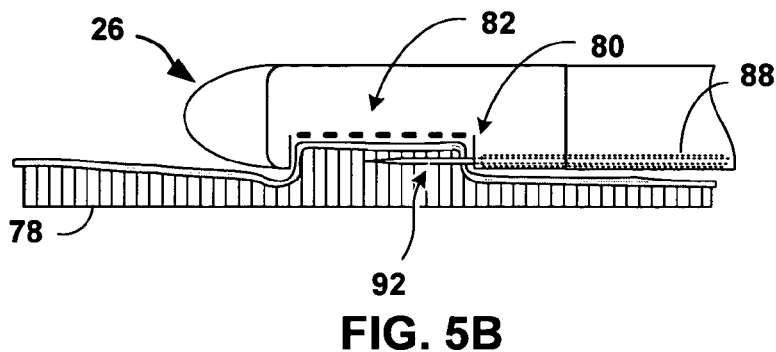

With tissue 78 drawn into cavity 80, a physician manipulates delivery instrument 26 to form a hole in the tissue with needle 92, as shown in FIG. 5B. The physician pushes needle 90 through sheath 88, thereby making the hole in the tissue drawn into cavity 80 and stabilized by vacuum ports 82.

Figure 5C:
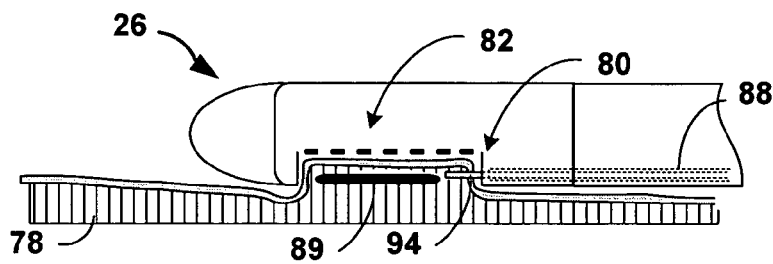
Figure 5D:
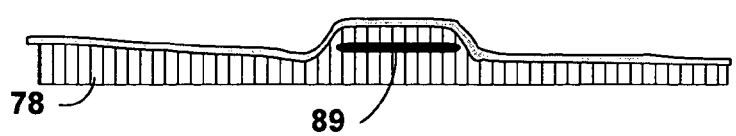

Insertion of needle 92 through tissue 100 causes needle 92 to form a pocket in the tissue. This pocket, which receives capsule 89, may be enlarged by injection of fluid, such as a saline solution, into the tissue 102. The physician withdraws needle assembly 90 from sheath 88, and inserts capsule 79 into sheath 88. The physician pushes capsule 79 through the hole and into the pocket in tissue 78 with pushrod assembly 94, as shown in FIG. 5C. After implanting capsule 79, the physician removes delivery instrument 26, and the capsule remains embedded within the exterior surface of the organ.

In certain embodiments, capsule 79 may comprise a therapeutic drug for treatment of physical conditions. exemplary classes of drugs include membrane channel drugs, antimuscarinic and channel blockers, antagonists, alpha adrenoceptor antagonists, beta adrenoceptor agonists, antidepressants, prostatglandin synthesis inhibitors, motor neuron suppression drugs, sensory desensitization drugs, anti-inflammatory drugs, hormones, muscarinic receptor agonists, anticholinesterase inhibitors, antibiotics, analgesic drugs, tricyclic antidepressants, muscle relaxants, anticholinergic, sensory desensitization drugs, anti-diarrheal drugs, motility inhibition drugs, motility stimulation drugs, tricyclic antidepressants, enzyme inhibitors, vascular dilators, smooth muscle relaxants, hormone replacements, selective serotonin reuptake inhibitors, tricyclic antidepressants and other drugs.

As another example, a radioactive isotope for implantation on or near a cancerous region of an organ, a polymer or other compound or material may be delivered. In some embodiments, capsule 79 may be an expandable hydrogel that expands to a larger sized due to reyhdration following implantation. Capsule 79 may be cylindrical, spherical, egg-shaped, or a partial cylinder for delivery through needle 92.

Figure 6:
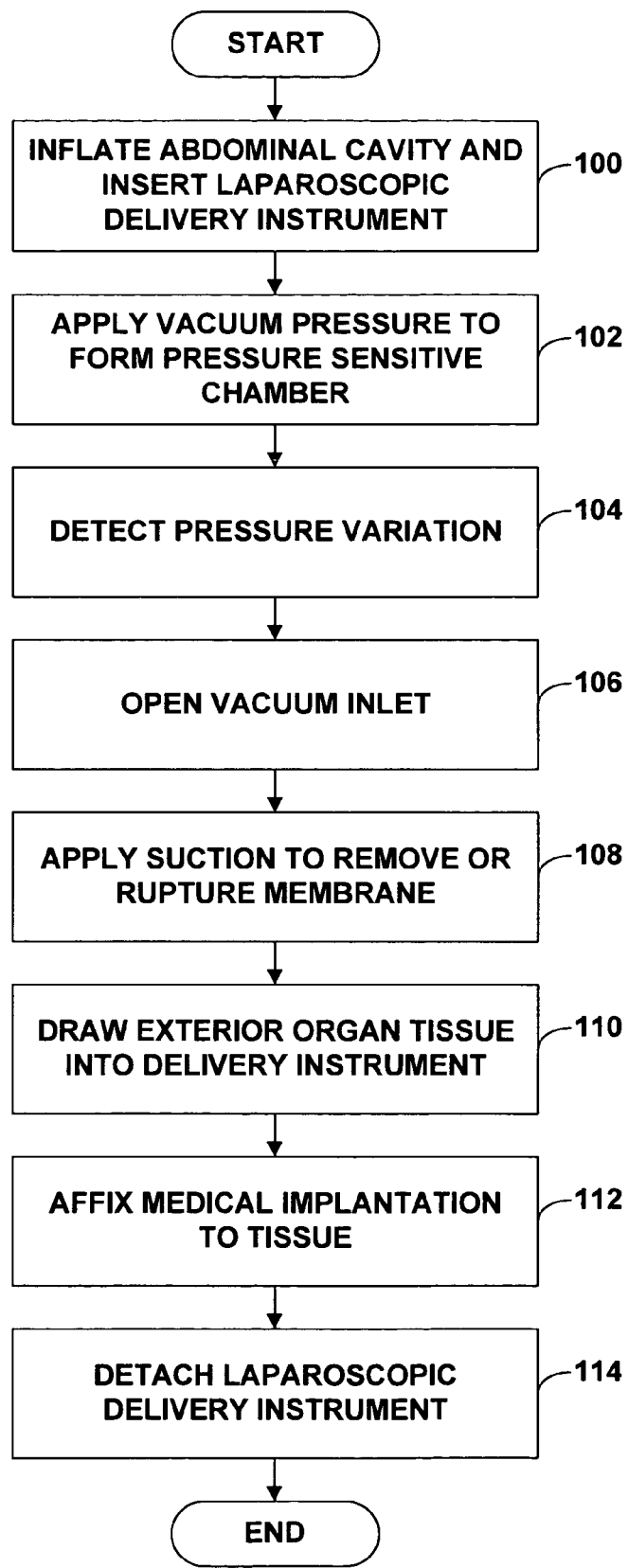
FIG. 6 is a flow diagram illustrating operation of a laparoscopic delivery instrument in which a medical implant is affixed to an exterior surface of an organ.

FIG. 6 is a flow diagram illustrating operation of delivery instrument 26 when used during laparoscopic surgery to deliver medical implant 11 to an exterior surface of an organ, such as stomach 12. In laparoscopic surgery, the patient receives general anesthesia and one or more small incisions are made in an abdomen of the patient. Initially, the abdomen is inflated with carbon dioxide so a surgeon can see the abdominal organs, and delivery instrument 26 is inserted within the abdominal cavity (100).

Next, vacuum source 20 applies vacuum pressure to delivery instrument 26, which forms a pressure sensitive chamber (102). As delivery instrument 26 enters the abdominal cavity and is forced against the exterior of a body organ, e.g., stomach 12, the pressure applied by the exterior surface deforms the distal end of the instrument, thereby causing a pressure variation within the pressure sensitive chamber. Delivery instrument 26 conveys the pressure variation to the physician via a display 32 to provide an indication of whether medical implant 11 is properly positioned against the exterior surface of the organ (104).

Once positioned, delivery instrument 26 opens vacuum inlet 23, which receives suction pressure from vacuum source 20 (106). The suction applied via the vacuum causes membrane 42 covering vacuum outlet 40 to rupture or be completely removed, in turn, opening vacuum outlet 40 (108). The suction applied by the vacuum further draws exterior tissue from the organ into a chamber of delivery instrument 26 (110). In embodiments of the invention, the exterior tissue may be drawn directly into delivery instrument 26 or through a void within medical implant 11.

Delivery instrument 26 affixes medical implant 11 to the drawn tissue using any of a variety of mechanisms (112). For example, delivering device 22 may advance a locking pin through the tissue drawn into the void of medical implant 11 to anchor medical implant 11 to the exterior surface of the organ, or may inject the medical implant within the tissue. Medical implant 11 is then detached from delivery instrument 26, thereby leaving medical implant 11 anchored to the organ (114).

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Several embodiments of the present invention are described above. It is to be understood that various modifications may be made to those embodiments of the present invention without departing from the scope of the claims. These and other embodiments are intended to fall within the scope of the appended claims.

The invention claimed is:

1. A method comprising:
    introducing a laparoscopic delivery instrument into a patient via an incision in an abdomen of the patient;
    applying vacuum pressure to an exterior surface of an organ to draw at least a portion of the exterior surface into a cavity of the laparoscopic delivery instrument; and
    affixing a medical implant to the portion of the exterior surface drawn into the cavity.

2. The method of claim 1, wherein applying vacuum pressure comprises applying the vacuum pressure to the exterior surface of the organ through a vacuum port of the medical implant.

3. The method of claim 1, wherein applying vacuum pressure comprises applying the vacuum pressure directly to the exterior tissue of the organ from a vacuum port associated with the laparoscopic delivery instrument.

4. The method of claim 1, wherein affixing a medical implant comprises anchoring the medical implant to the portion of the exterior surface drawn into the cavity of the laparoscopic delivery instrument.

5. The method of claim 1, wherein the implant includes an electrode.

6. The method of claim 5, wherein the electrode includes an elongated lead carrying an electrical conductor, wherein the electrode receives electrical stimulation energy from an implantable medical device via the electrical conductor.

7. The method of claim 1, wherein the medical implant includes a diagnostic sensor.

8. The method of claim 1, wherein affixing a medical implant comprises:
    forming a hole in the portion of the exterior surface disposed in the cavity of the laparoscopic delivery instrument; and
    implanting the medical implant within the hole formed within the exterior surface.

9. The method of claim 8, wherein the medical implant comprises one of a radioactive isotope, a biologic, a therapeutic drug or a polymer.

10. The method of claim 1, wherein affixing a medical implant comprises securing the medical implant into the portion of the exterior surface drawn into the cavity of the laparoscopic delivery instrument.

11. The method of claim 1, wherein affixing a medical implant comprises securing the medical implant with a surgical adhesive to the portion of the exterior surface drawn into the cavity of the laparoscopic delivery instrument.

12. The method of claim 1, wherein affixing a medical implant comprises affixing the medical implant to the portion of the exterior surface drawn into the cavity of the laparoscopic with a helical anchor or a staple.

13. The method of claim 1, wherein the organ comprises a stomach, a bladder or a kidney.

14. The method of claim 1, further comprising:
    accessing an abdominal cavity of a patient through the incision in the abdomen of the patient;
    inserting the laparoscopic delivery instrument within the abdominal cavity;
    moving the laparoscopic delivery instrument to a position proximate to the exterior surface of the organ; and
    activating a vacuum source to draw the portion of the exterior surface through a void within the medical implant and into the laparoscopic delivery instrument.

15. The method of claim 1, wherein the medical implant comprises a radioactive isotope.

16. A laparoscopic system for delivering a medical implant to an external surface of an organ, the laparoscopic system comprising:
    means for introducing a laparoscopic delivery instrument into a patient via an incision in an abdomen of the patient;
    means for applying vacuum pressure to an exterior surface of an organ to draw at least a portion of the exterior surface into a cavity of the laparoscopic delivery instrument; and
    means for affixing a medical implant to the portion of the exterior surface drawn into the cavity.

17. The system of claim 16, further comprising means for applying the vacuum pressure to the exterior surface of the organ through a vacuum port of the medical implant.

18. The system of claim 16, further comprising means for applying the vacuum pressure directly to the exterior tissue of the organ from a vacuum port associated with the laparoscopic delivery instrument.

19. The system of claim 16, further wherein the affixing means comprises means for anchoring the medical implant to the portion of the exterior surface drawn into the cavity of the laparoscopic delivery instrument.

20. The system of claim 16, wherein the implant includes one or more of an electrode carrying a lead, a wireless electrode, a diagnostic sensor, an isotope, a therapeutic drug, or a polymer.

21. The system of claim 16, wherein the affixing means comprises:

means for forming a hole in the portion of the exterior surface disposed in the cavity of the laparoscopic delivery instrument; and means for implanting the medical implant within the hole formed within the exterior surface.

\* \* \* \* \*

UNITED STATES PATENT AND TRADEMARK OFFICE
CERTIFICATE OF CORRECTION

PATENT NO.      : 7,593,777 B2                                    Page 1 of 1
APPLICATION NO. : 10/973944
DATED           : September 22, 2009
INVENTOR(S)     : Martin T. Gerber It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1366 days.

Signed and Sealed this

Twenty-eighth Day of September, 2010

David J. Kappos
*Director of the United States Patent and Trademark Office*